United States Patent [19]

Steffan

[11] Patent Number: 5,723,613
[45] Date of Patent: Mar. 3, 1998

[54] PROCESS FOR THE FREE-RADICAL CHLORINATION OR BROMINATION OF METHYL AROMATIC COMPOUNDS

[75] Inventor: Guido Steffan, Odenthal, Germany

[73] Assignee: Bayer Aktiengesellschaft, Leverkusen, Germany

[21] Appl. No.: 956,126

[22] Filed: Oct. 2, 1992

[30] Foreign Application Priority Data

Oct. 11, 1991 [DE] Germany .............. 41 33 676.3

[51] Int. Cl.$^6$ .............. C07D 241/36; C07C 22/00; C07C 17/00; C07C 51/58
[52] U.S. Cl. .............. 544/356; 544/353; 562/840; 562/849; 562/864; 562/834; 570/144; 570/198
[58] Field of Search .............. 570/197, 196, 570/198, 144; 544/356, 353; 562/840, 849, 864, 834

[56] References Cited

U.S. PATENT DOCUMENTS

| | | | |
|---|---|---|---|
| 3,230,268 | 1/1966 | Kobayashi | 570/197 |
| 4,046,656 | 9/1977 | Davis et al. | |
| 4,439,620 | 3/1984 | Klauke et al. | |
| 4,950,813 | 8/1990 | Döscher et al. | |

FOREIGN PATENT DOCUMENTS

| | | | |
|---|---|---|---|
| 0306804 | 8/1988 | European Pat. Off. | |
| 3039884 | 10/1980 | Germany | |
| 3142856 | 10/1981 | Germany | |
| 43-8254 | 3/1968 | Japan | 570/197 |
| 2240031 | 9/1990 | Japan | 570/197 |

OTHER PUBLICATIONS

Houben–Weyl, Methoden der Org. Chemie, V/III, pp. 716, 1962.
German Patent Specification 234,290, Mar. 27, 1909, p. 116.
J. Chem. Soc. 121, Aug. 8, 1922, pp. 2212–2215.

*Primary Examiner*—Alan Siegel
*Attorney, Agent, or Firm*—Sprung Kramer Schaefer & Briscoe

[57] ABSTRACT

Methyl aromatic compounds of the formula (I)

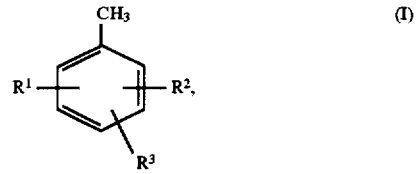

in which $R^1$, $R^2$ and $R^3$ have the meaning given in the description,
can be reacted in an advantageous manner using free-radicals to give the associated trichloromethyl or tribromomethyl aromatic compounds, if the reaction is carried out in the presence of one or more chlorides or bromides of the heavy alkali metals.

14 Claims, No Drawings

PROCESS FOR THE FREE-RADICAL CHLORINATION OR BROMINATION OF METHYL AROMATIC COMPOUNDS

BACKGROUND OF THE INVENTION

1. Field of the Invention

The invention relates to a free-radical process for the side chain chlorination or side chain bromination of methyl aromatic compounds of the type described below, in which any sulphonyl halide groups which may be present are converted with the elimination of sulphur dioxide into halide located on the nucleus.

2. Description of the Related Art

The side chain halogenation of methyl aromatic compounds, for example the side chain chlorination to give the corresponding trichloromethyl aromatic compounds, is well known, as is the decomposition of aromatic sulphonyl halides, for example aromatic sulphonyl chlorides, to give the corresponding aryl halides (Houben-Weyl, Methoden der Org. Chemie [Methods of organic chemistry], volume V/III p. 716). Both processes proceed by a free-radical mechanism and are carried out in industrial chemistry under illumination, with addition of free-radical generators or purely thermally. Free-radical generators are for example phosphorus pentachloride, sulphuryl chloride, sulphur chlorides, iodine, peroxides and azo compounds. During the side chain halogenation, the benzyl stage, the benzal stage and finally the benzotrihalide stage are attained sequentially, but partially overlapping. In particular, to attain the benzotrihalide stage, relatively long reaction times and excesses of halogen are required; for this reason, for example in the continuous side chain chlorination of toluene, the chlorine is conducted in countercurrent to the liquid toluene.

The simultaneous decomposition of a sulphonyl chloride group with elimination of $SO_2$ and the chlorination of a methyl group to give the trichloromethyl group are also already known (preparation of 2,4-dichlorobenzo-trichloride from 2-chloro-toluene-4-sulphonyl chloride: German Patent Specification 234,290; Frdl 10, 116). In this case, however, neither the reaction times nor yields, qualities or extent of the excess of chlorine required are given. Neither is anything stated on the size of the reaction batch.

The preparation of 4-trichloromethyl-benzoyl chloride by chlorination of 4-methyl-benzoyl chloride under illumination is described in J. Chem. Soc. (London) 121, 2212 to 2214. In EP 306,804, the preparation of the same compound by means of a 40-hour chlorination with catalysis by di-lauroyl peroxide in a moderate yield (90%) is described.

The preparation of 2,3-dichloro-6-trichloromethyl-quinoxaline by means of an 80 to 110-hour chlorination in a large amount of o-dichlorobenzene as solvent is described in German Offenlegungsschrift 3,039,884. The product is obtained here both in moderate quality (93%) and in moderate yield (92.5%).

The preparation of 2,4-dichloro-5-fluoro-benzotrichloride is described in German Offenlegungsschrift 3,142,856. In this case, 2,4-dichloro-5-fluoro-toluene, obtained by diazotisation and subsequent fluorination of 3-amino-4,6-dichlorotoluene, is chlorinated under illumination. The end product is obtained in a yield of 85% of the theoretical yield; reaction times are not given in this case.

The benzotrihalides, in particular the benzotrichlorides, having different substituents are required in many cases as precursors, for example for the hydrolysis to give the corresponding carboxylic acids or the carboxylic acid halides and also for a series of condensation reactions. Obtaining them by free-radical halogenation, for example by means of free-radical chlorination, has hitherto only been possible in an unsatisfactory manner, since the halogenation, in particular in the conversion from the benzal stage to the benzotrihalide stage, requires a great deal of time and demands high excesses of chlorine (compare the abovementioned individual examples). If it is attempted to reduce the halogenation time at elevated temperatures, a noticeable fraction of the trihalide groups is eliminated, and the yield and content of the end product is thereby reduced. Moreover, under drastically intensified reaction conditions, the formation of products halogenated at the nucleus begins, which further adversely affects the quality of the end product.

Whereas, with small laboratory batches with about 0.5 mol of starting material and with the use of conventional free-radical initiators, chlorination times, which are still acceptable, of about 15 to 20 hours are achieved, with larger batches on the industrial scale, the necessary chlorination times increase drastically. Even the laboratory batches mentioned require in this case, however, amounts of chlorine in the range of 5.5 to 8 mol per mole of starting material, whereas the theoretical value is 3 mol of chlorine per mole of starting material. For the abovementioned case of the simultaneous free-radical elimination of $SO_2$ from a sulphonyl halide group in addition to the side chain halogenation, the $SO_2$ formed fundamentally retards the halogenation. With small laboratory batches, the $SO_2$ can be driven off by means of surplus halogen vapour; this driving-off becomes increasingly ineffective as the batch size is increased. Thus, on the basis of laboratory results, a pure chlorination time of about 80 to 100 hours has been estimated for chlorination in a 6 $m^3$ chlorination reactor. The alternative, comprising use of extreme excesses of chlorine, has to be ruled out on ecological grounds and would only cause a slight improvement in any case.

SUMMARY OF THE INVENTION

It has now, surprisingly, been found that the free-radical side chain halogenation can be influenced in an advantageous manner by the addition of one or more halides of the heavy alkali metals. In this case, shorter reaction times are also attainable with only moderate excesses of halogen. Yield and quality of the halogenation product are very good.

The invention therefore relates to a process for the free-radical chlorination or bromination of methyl aromatic compounds of the formula (I)

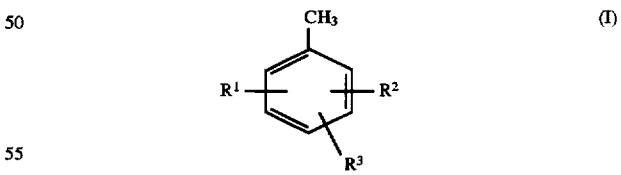

in which $R^1$ and $R^2$ independently of each other denote hydrogen, halogen, COHal or $SO_2$Hal and $R^3$ is hydrogen, halogen or COHal, where $R^2$ and $R^3$ together, if they are adjacent, can form the radical of a 5- or 6-membered isocyclic or heterocyclic ring, which can itself be monosubstituted or di-substituted by halogen, COHal or $SO_2$Hal, where such heterocyclic rings contain 1 or 2 hetero atoms selected from the group comprising N, O and S, to give trichloromethyl aromatic compounds or tribromomethyl aromatic compounds of the formula (II)

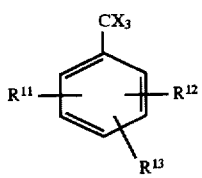

(II)

in which $R^{11}$ and $R^{12}$ independently of each other denote hydrogen, halogen or COHal, $R^{13}$ is hydrogen, halogen or COHal, where $R^2$ and $R^3$, if they are adjacent, can form the radical of a 5- or 6-membered isocyclic or heterocyclic ring, which itself can be monosubstituted or disubstituted by halogen or COHal, where such heterocyclic rings contain 1 or 2 hetero atoms selected from the group comprising N, O and S, and X is chlorine or bromine, and where, in the case of the occurrence of $SO_2Hal$ groups, these are converted to halogen with elimination of $SO_2$, which is characterised in that the halogenation is carried out in the presence of one or more alkali metal halides selected from the group comprising KCl, KBr, KI, RbCl, RbBr, RbI, CsCl, CsBr and CsI.

In a preferred manner, of the mentioned halides of the heavy alkali metals, the chlorides and bromides are used.

To avoid an unwanted halogen exchange, it is further advantageous in the case of a chlorination to use one or more of the alkali metal chlorides mentioned, and in the case of a bromination to use one or more of the alkali metal bromides mentioned. In a preferred manner, the halides mentioned of potassium and caesium are used, a mixture of potassium halide and caesium halide, in the case of a chlorination therefore a mixture of KCl and CsCl, is particularly preferably used. The amount of the alkali metal halide to be used is 0.1–30 mmol per mole of the methylaromatic compound to be halogenated.

In order to prevent the alkali metal halides from sintering together or accumulating to give spherical structures during the halogenation, it has proved advantageous to add to the salts an inert solid, which to some extent assumes the function of a support. Such inert solids are for example Celite. The amount of this inert solid added is approximately 50–200% of the amount of alkali metal halide used.

In a further advantageous manner, a tertiary amine having adequate stability under the halogenation conditions, for example pyridine, is added to the reaction mixture in an amount of approximately 0.1–2 g, preferably approximately 0.5 g per mole of methylaromatic compound. The mode of action of the tertiary amine is to be compared with that of a cocatalyst.

Halogen or Hal in formula (I) denotes independently of each other fluorine, chlorine or bromine, preferably fluorine or chlorine.

The methylaromatic compounds to be halogenated are generally present in an impure form from their preparation.

Such impurities are for example residues of thionyl chloride from the introduction of other functional groups or decomposition products of the most diverse types. These impurities normally adversely affect the free-radical halogenation, so that, in conventional free-radical side chain halogenations, the starting materials have to be purified in advance by means of distillation, crystallisation, filtration or other measures. It is a further advantage of the process according to the invention that such a prepurification of the starting material is not required.

The process according to the invention is carried out in a preferred manner as chlorination, a mixture of KCl and CsCl preferably being used in the manner described above.

The methylaromatic compound used is, in a preferred manner, a compound of the formula (III)

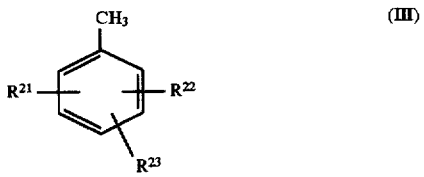

in which $R^{21}$ and $R^{22}$ independently of each other denote hydrogen, fluorine, chlorine, COF, COCl, $SO_2F$ or $SO_2Cl$ and $R^{23}$ denotes hydrogen, F or Cl, where $R^{22}$ and $R^{23}$ together denote the radical of a 6-membered aromatic N-heterocycle, which can contain a further N-atom as second hetero atom, where the heterocycle can be monosubstituted or disubstituted by fluorine or chlorine.

In a particularly preferred manner, the methylaromatic compound used is a compound of the formula (IV)

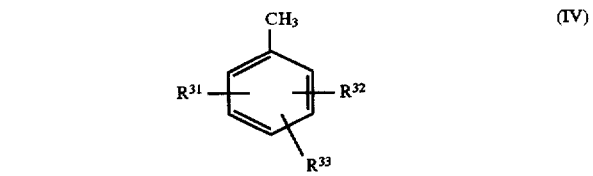

in which $R^{31}$ and $R^{32}$ independently of each other denote hydrogen, chlorine, COCl or $SO_2Cl$ and $R^{33}$ is hydrogen, fluorine or chlorine, where $R^{32}$ and $R^{33}$ together denote the radical of the quinoxaline ring, which can be substituted in the 2- and/or 3-position by fluorine or chlorine.

The course of the reaction is clarified with important examples by means of the following chemical equations:

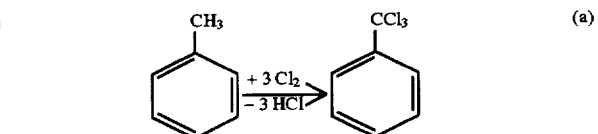

(a)

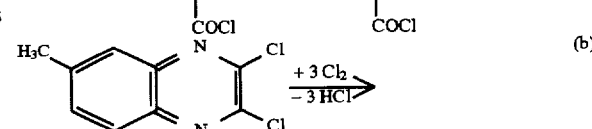

(b)

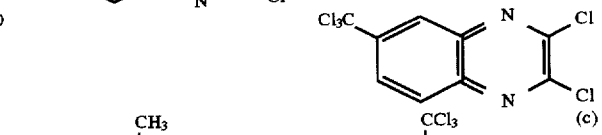

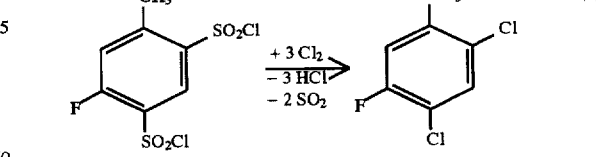

(c)

The process according to the invention is carried out at a temperature of 120°–240° C., preferably 160°–220° C. and at a pressure of 0.5–5 bar, preferably of 1–1.5 bar. The reaction times are dependent in a manner known to those skilled in the art on the size of the reaction batch, but in general are only approximately 25 to 85% of the time which is necessary without the catalysis according to the invention.

EXAMPLES

Example 1

2,4-Dichloro-5-fluoro-benzotrichloride 970 g of crude 5-fluorotoluene-2,4-disulphonyl chloride, prepared by the method described in EP 202.493 (corresponding to 3.0 mol of pure product and 3.1 mol of the m-fluorotoluene used for the disulphonyl chloride preparation), were mixed, in the molten condition, with 0.5 g of CsCl 4.5 g of KCl and 3 g of Celite.

A total of 1,400 g of chlorine was passed in in a total of 23 hours according to the following scheme:

400 g of chlorine at 160° to 180° C. in 5 hours 800 g of chlorine at 180° to 197° C. in 12 hours 200 g of chlorine at 197° to 195° C. in 6 hours.

After chlorination is complete, according to the gas chromatogram the crude product contained approximately 89% of 2,4-dichloro-5-fluoro-benzotrichloride approximately 1.8% of 2,4-dichloro-5-fluoro-benzal chloride approximately 3.1% of 1,2,4-trichloro-5fluorobenzene approximately 2% of diverse traces (not completely determined)

(in addition, approximately 4% of separately determined involatile fractions).

By means of a work-up by distillation, after separating off the trichlorofluorobenzene first fraction, 1. 15 g of the abovementioned benzal chloride were obtained (approximately 2% of theory), which were added to the next batch and 2. 768 g of the desired benzotrichloride were obtained having the following composition:
   0.5% of 2,4-dichloro-5-fluoro-benzal chloride
   98.2% of 2,4-dichloro-5-fluoro-benzotrichloride
   1.3% of various unknown substances.

This corresponds to a yield of 89% of the theoretical yield, which increases to approximately 91% of the theoretical yield by the abovementioned recycling of the benzal chloride into the subsequent batches.

Example 1a (Comparison Example, not claimed)

The same starting material in the same quantity was used as in Example 1. Instead of CsCl/KCl/Celite, 19 g of $PCl_5$ were used as catalyst (added in several portions). As a result of the significantly slower chlorine uptake, a total of 2,945 g of chlorine was passed through in a total of 48 hours according to the following scheme:

600 g of chlorine at 170° to 195° C. in 10 hours 1,200 g of chlorine at 195° to 200° C. in 26 hours 245 g of chlorine at 198° to 200° C. in 12 hours.

After work-up of the reaction mixture (according to the gas chromatogram:

2.2% of 2,4-dichloro-5-fluoro-benzal chloride 86.5% of 2,4-dichloro-5-fluoro-benzotrichloride 3.2% of 1,2,4-trichloro-5-fluorobenzene approximately 4% of diverse traces, not completely determined in addition, approximately 4% of separately determined involatile fractions)

there were obtained—as described in Example 1— approximately 86% of the theoretical yield of the abovementioned benzotrichloride and 2.5% of the theoretical yield of the abovementioned benzal chloride.

On recycling the benzal chloride to the subsequent batches, a total yield of approximately 88.5% of the theoretical yield of the abovementioned benzotrichloride was obtained.

Example 2

2,4-Dichloro-5-fluoro-benzotrichloride (Industrial Example)

2,750 kg of m-fluorotoluene were metered into 5,860 kg of chlorosulphonic acid, situated in the reactor, in the course of 8 hours, the temperature with HCl formation rising to 70° C.; the mixture was then heated to 90° C. in a further 2 hours.

In the course of 4 hours, approximately 1,000 kg of chlorosulphonic acid/thionyl chloride distillate from a preceding lot were then metered in (containing approximately 600 kg of chlorosulphonic acid and 400 kg of thionyl chloride); a further 4,100 kg of thionyl chloride were then metered in at 90° C. in the course of 18 hours; the mixture was then heated in 3 hours to 155° C., held at this temperature for 2 hours, then cooled to 120° C.

At this temperature a further 2,200 kg of thionyl chloride were metered in in 9 hours.

After a further reaction time of 3 hours approximately 1,000 kg of excess chlorosulphonic acid/thionyl chloride mixture were distilled off in vacuo to a bottom temperature of 160° C. and were reused in the following lot—as described above. About 7,650 kg of crude 5-fluorotoluene-2,4-disulphonyl chloride were obtained, which was used in the chlorination without further treatment. (The yield, relative to m-fluorotoluene, was about 97 to 98% of the theoretical yield).

10 kg of KCl, 7 kg of Celite and 0.15 kg of CsCl were added, heated to 165° C. and then a total of 7,200 kg of chlorine were passed in according to the following scheme:

4,800 kg of chlorine at 165° to 195° C. in 14 hours 1,600 kg of chlorine at 195° to 210° C. in 7 hours 800 kg of chlorine at 210° to 205° C. in 8 hours.

Before passing in the last 800 kg of chlorine, the intermediate fraction from the distillation of the previous lot (approximately 800 kg having a content of 30 to 40% of dichlorofluorobenzal chloride) are added to the lot.

(Care should be taken that, when 180° C. has been attained in the abovementioned chlorination, at least 1,400 kg of chlorine have already been passed in, since otherwise the reaction mixture has a tendency to degrade. This degradability disappears gradually with increasing chlorine content.)

In the subsequent work-up by distillation, approximately 130 kg (2.5% of the theoretical yield) of trichlorofluorobenzene were initially obtained as first fraction, then 800 kg of intermediate fraction (having a content of 30 to 40% of dichlorofluorobenzal chloride) and finally approximately 6,685 kg of dichlorofluorobenzotrichloride were obtained having the following composition:

99.3% of 2,4-dichloro-5-fluoro-benzotrichloride 0.2–0.3% of 2,4-dichloro-5-fluoro-benzal chloride 0.2% of isomeric dichlorofluoro-benzal chloride and diverse traces.

This corresponded to a yield of approximately 94% of the theoretical yield, relative to m-fluorotoluene or a yield of approximately 96% of the theoretical yield, relative to the 5-fluorotoluene-2,4-disulphonyl chloride.

Approximately 200 kg remained as distillation residue.

Without addition of caesium chloride, particularly in the chlorination on an industrial scale, the formation of a high-melting sublimate deposit in the vapour tube and condenser is all too obvious.

Example 3

4-Trichloromethyl-benzoyl chloride

4-Methylbenzoyl chloride was prepared in a conventional manner from 4-methylbenzoic acid and thionyl chloride and after excess thionyl chloride was distilled off, was used as the crude product in the side chain chlorination.

1,097 g of crude 4-methylbenzoyl chloride, 99.85% pure, (corresponding to 7.0 mol) were mixed with 2 g of caesium chloride and 3.5 g of pyridine and were chlorinated according to the following scheme:

The following were passed in with intensive stirring 1,200 g of chlorine at 195° to 200° C. in 14 hours 450 g of chlorine at 200° to 210° C. in 5 hours 250 g of chlorine at 210° to 215° C. in 5 hours.

1,798 g of chlorination product were obtained having a content of 98.2% (according to the gas chromatogram) of 4-trichloromethyl-benzoyl chloride. After vacuum distillation, 1,763 g of product were obtained having a content of 99.2% of 4-trichloromethyl-benzoyl chloride (according to the gas chromatogram), which corresponds to a yield of 96.9% of the theoretical yield.

Example 3a (Comparison Example, not claimed)

A chlorination carried out in the same manner as in Example 3, but without addition of caesium chloride, required 28 hours of chlorination time and produced 1,788 g of crude product having a content of 95.4% of 4-trichloromethylbenzoyl chloride (according to the gas chromatogram).

After vacuum distillation, 1,754 g of product were obtained having a content of 96.8% of 4-trichloromethyl-benzoyl chloride (according to the gas chromatogram), which corresponds to a yield of 94% of the theoretical yield. (The product contained small amounts of by-products, apparently chlorinated on the nucleus.)

Example 4

2,3-Dichloro-6-trichloromethyl-quinoxaline 2,3-Dichloro-6-methyl-quinoxaline was prepared by condensation of oxalic acid with 3,4-diamino-toluene and subsequent reaction with thionyl chloride and was used as the crude product (after distilling off excess thionyl chloride) in the chlorinations.

880 g of 96.1% pure crude substance (3.97 mol) were mixed with 2 g of KCl 1 g of CsCl 2 g of Celite 2 g of pyridine and 30 g of chlorobenzene (to avoid sublimate deposit in the condenser)

and were chlorinated according to the following scheme:

The following were passed in with intensive stirring 870 g of chlorine at 135° to 160° C. in 9 hours 280 g of chlorine at 160° to 190° C. in 2.5 hours 150 g of chlorine at 190° to 200° C. in 2.5 hours.

The gas chromatogram of the crude product (1,334 g) showed a content of 95.3% of 2,3-dichloro-6-trichloromethyl-quinoxaline and 0.3% of 2,3-dichloro-6-dichloromethyl-quinoxaline in addition to some high boilers (total 3.5%) and approximately 1% of separately determined involatile fractions.

After vacuum distillation, 1,252 g of distillate were obtained having a content of 96.8% of 2,3-dichloro-6-trichloromethyl-quinoxaline, which corresponds to a yield of 98.5% of the theoretical yield.

Example 4a (Comparison Example, not claimed)

The chlorination was carried out in the same manner as described in Example 4, but, as catalyst, only 2 g of pyridine were added and no CsCl, KCl or Celite.

The chlorination necessitated a time of 20 hours (instead of 14 hours) and required in total 1,580 g of chlorine (instead of 1,300 g).

1,325 g of crude product were obtained having a content (according to the gas chromatogram) of 90.2% of 2,3-dichloro-6-trichloromethyl-quinoxaline 0.8% of 2,3-dichloro-6-dichloromethyl-quinoxaline in addition to a plurality of high boilers (total: 7.1%) and approximately 2% of separately determined involatile fractions.

After vacuum distillation, 1,255 g of distillate were obtained having a content of 93.8% of 2,3-dichloro-6-trichloromethyl-quinoxaline, which corresponds to a yield of 93.7% of the theoretical yield.

What is claimed is:

1. A process for the free-radical chlorination or bromination of a methylaromatic compound of the formula

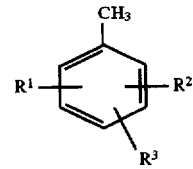

in which $R^1$ and $R^2$ independently of each other denote hydrogen, halogen, COHal or $SO_2$Hal and $R^3$ denotes hydrogen or halogen, where $R^2$ and $R^3$ together, if they are adjacent, can form the radical of a 5- or 6-membered isocyclic or heterocyclic rings which can itself be mono-substituted or disubstituted by halogen, COHal or $SO_2$Hal, where such heterocyclic rings contain 1 or 2 hetero atoms selected from the group comprising N, O and S, to give a trichloromethyl aromatic compound or a tribromomethyl aromatic compound of the formula

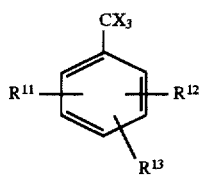

in which
- $R^{11}$ and $R^{12}$ independently of each other denote hydrogen, halogen or COHal,
- $R^{13}$ is hydrogen, halogen or COHal, where $R^{12}$ and $R^{13}$, if they are adjacent, can form the radical of a 5- or 6-membered isocyclic or heterocyclic ring, which itself can be monosubstituted or disubstituted by halogen or COHal, where such heterocyclic rings contain 1 or 2 hereto atoms selected from the group comprising N, O and S, and
- X is chlorine or bromine, and where, in the case of the occurrence of $SO_2Hal$ groups, these are converted to halogen with elimination of $SO_2$, without ultraviolet irradiation and without the addition of free-radical generators, wherein the halogenation is carried out at a temperature of 120°–240° C. and in the presence of one or more alkali metal halides selected from the group comprising KCl, KBr, RbCl, RbBr, CsCl and CsBr in an amount of 0.1–30 mmol of alkali metal halide per mol of the methylaromatic compound, provided that when X is chlorine, only the alkali metal chlorides are used, and when X is bromine, only the alkali metal bromides are used.

2. The process of claim 1, wherein the alkali metal halides are the halides of K and Cs.

3. The process of claim 2, wherein a mixture of halides of K and Cs are used.

4. The process of claim 1, wherein a chlorination of the methyl group is carried out.

5. The process of claim 4, wherein a mixture of KCl and CsCl is used.

6. The process of claim 1, wherein the methylaromatic compound used is a compound of the formula

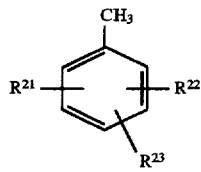

in which
- $R^{21}$ and $R^{22}$ independently of each other denote hydrogen, fluorine, chlorine, COF, COCl, $SO_2F$ or $SO_2Cl$ and
- $R^{23}$ denotes hydrogen, fluorine or chlorine, where $R^{22}$ and $R^{23}$ together denote the radical of a 6-membered aromatic N-heterocycle, which can contain a further N-atom as second hetero atom.

7. The process of claim 6, wherein the methylaromatic compound used is a compound of the formula

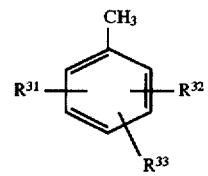

in which
- $R^{31}$ and $R^{32}$ independently of each other denote hydrogen, chlorine, COCl or $SO_2Cl$ and
- $R^{33}$ is hydrogen, fluorine or chlorine, where $R^{32}$ and $R^{33}$ together denote the radical of the quinoxaline ring, which can be substituted in the 2- and/or 3-position by fluorine or chlorine.

8. The process of claim 1, wherein one or more alkali metal halides are used together with an inert solid in an amount of 50–200% of the amount of alkali metal halide used.

9. The process of claim 1, wherein one or more of the alkali metal halides are used together with an amine in an amount of 0.1–2 g per mol of methylaromatic compound.

10. The process of claim 1, wherein the methylaromatic compound to be chlorinated or brominated is used in the form of a crude product from its preparation without previous purification.

11. The process of claim 1, which is carried out at a temperature of 120°–240° C. and at a pressure of 0.5–5 bar.

12. The process of claim 11, which is carried out at 160°–220° C.

13. The process of claim 11, which is carried out at 1–1.5 bar.

14. The process of claim 9, wherein said amine is pyridine.

* * * * *